United States Patent [19]

Kleschick

[11] Patent Number: 4,822,404

[45] Date of Patent: Apr. 18, 1989

[54] SULFONAMIDES DERIVED FROM SUBSTITUTED 2-AMINO-1,2,4-TRIAZOLO (1,5-A) PYRIMIDINES AND COMPOSITIONS AND METHODS OF CONTROLLING UNDESIRED VEGETATION

[75] Inventor: William A. Kleschick, Martinez, Calif.

[73] Assignee: The Dow Chemical Company, Midland, Mich.

[21] Appl. No.: 111,003

[22] Filed: Oct. 20, 1987

Related U.S. Application Data

[63] Continuation of Ser. No. 773,406, Sep. 6, 1985, abandoned which is a continuation-in-part of Sec. No. 574,232, 1/26, 1984, abandoned.

[51] Int. Cl.$^4$ ................... A01N 43/90; C07D 487/04
[52] U.S. Cl. ..................................... 71/92; 544/263; 548/267
[58] Field of Search ..................... 544/263; 71/92

[56] References Cited

U.S. PATENT DOCUMENTS

| | | | |
|---|---|---|---|
| 2,875,125 | 2/1959 | Gaertner | 71/92 |
| 3,637,366 | 1/1972 | Wietelmann et al. | 71/92 |
| 4,411,690 | 10/1983 | Tseng | 544/255 |
| 4,638,075 | 1/1987 | Kleschick | 544/263 |
| 4,740,233 | 4/1988 | Kleschick | 544/263 |

FOREIGN PATENT DOCUMENTS

| | | | |
|---|---|---|---|
| 58-31894 | 10/1973 | Japan | 71/92 |
| 58-69803 | 4/1983 | Japan | |

OTHER PUBLICATIONS

Kreutzberger, A. Chem. Ber. 1966, 99, 2237.

Primary Examiner—Donald G. Daus
Assistant Examiner—Mark W. Noel
Attorney, Agent, or Firm—Merlin B. Davey; D. Wendell Osborne

[57] ABSTRACT

Novel compounds, e.g., N-(5,7-dimethyl-1,2,4-triazolo [1,5-a]pyrimidin-2-yl)-2-thiophene sulfonamide and their compositions and use in the control of weeds.

9 Claims, No Drawings

SULFONAMIDES DERIVED FROM SUBSTITUTED 2-AMINO-1,2,4-TRIAZOLO (1,5-A) PYRIMIDINES AND COMPOSITIONS AND METHODS OF CONTROLLING UNDESIRED VEGETATION

CROSS-REFERENCE TO RELATED APPLICATION

This is a continuation of application Ser. No. 773,406, filed Sept. 6, 1985, now abandoned which is a continuation-in-part of Application Ser. No. 574,232 filed Jan. 26, 1984 now abandoned.

BACKGROUND OF THE INVENTION

In recent years there has been a great deal of effort directed to the development of sulfonamides having herbicidal activity and several of these compounds have reached the stage of commercialization, i.e., chlorsulfuron and sulfometuron methyl. These compounds exhibit both preemergence and postemergence activity against undesirable vegetation and, in additon, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; O,O-diisopropyl phosphorodithioate-S-ester with N-(2-mercaptoethyl)benzenesulfonamide; 3-isopropyl-1H-2,1,3-benzothiadiazin-4(3H)-one 2,2-dioxide; N-[2,4-dimethyl-5-[[(trifluoromethyl)sulfonyl]amino]phenyl]acetamide; and 3,5-dinitro-$N^4,N^4$-dipropylsulfanilamide.

SUMMARY OF THE INVENTION

I have now found that compounds having the formula:

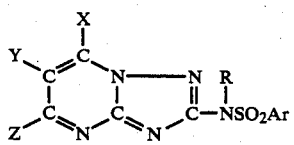

(I)

wherein R represents hydrogen, alkyl, alkenyl, alkynyl,phenylalkyl, substituted phenylalkyl, acyl, alkoxycarbonyl, phenyloxycarbonyl, dialkylaminocarbonyl, alkylsulfonyl, phenylsulfonyl, alkylthocarbonyl or phenylthiocarbonyl, each contaning one to ten carbon atoms, Ar represents a substituted or unsubstituted mono or bicyclic aromatic or heteroaromatic (containing one or more or a combination of N, O or S atoms) ring system containing five or six-membered rings or the pyrimidine ring is reduced to form a 4,5,6,7-tetrahydro-1,2,4-triazolo[1,5-a]pyrimidine ring are active herbicides and are readily produced.

DETAILED DESCRIPTION OF THE INVENTION

The aromatic or heteroaromatic ring systems include, for example, phenyl; 1- or 2-naphthyl; 2-, 3- or 4-pyridyl; 2- or 3-thienyl; 2- or 3-furyl; 2-, 4- or 5thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazoly; 2-benzimidazolyl and 1-benztriazolyl. Typical examples of substituents found on the aromatic or heteroaromatic ring systems may be one, more than one or a combination of the following: halo (F, Cl, Br, I), $C_1$–$C_6$ alkyl, $C_1$–$C_6$ haloalkyl, phenyl, hydroxy, $C_1$–$C_6$ alkoxy, $C_1$–$C_6$ haloalkoxy phenoxy, substituted phenoxy, heteroaryloxy, substituted heteroaryloxy, amino, $C_1$–$C_6$ alkylamino, $C_1$–$C_6$ dialkylamino, nitro, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, substituted or unsubstituted phenylthio, substituted or unsubstituted phenylsulfinyl, substituted or unsubstituted phenylsulfonyl, cyano, carboxylic acids (and derivatives of carboxylic acids such as esters derived from readily available alcohols and amides derived from ammonia or readily available primary and secondary amines), sulfonic acid (and derivatives of sulfonic acids such as sulfonates derived from readily available alcohols and sulfonamides derived from ammonia or readily available primary or secondary amines), formyl, $C_1$–$C_6$ alkylcarbonyl, $C_1$–$C_6$ haloalkylcarbonyl, phenylcarbonyl, substituted phenylcarbonyl, oximino,oxime ethers, carbinols (and carbinol derivatives such as ethers and esters derived from readly availale alkylating agents and carboxylic acids respectively) and $C_1$–$C_6$ mercaptoalkyl (and derivatives of mercaptoalkyl groups such as thioethers and thioesters derived from readily available alkylating agents and carboxylic acids respectively).

The substituents on the triazolopyrimidine fragment of structure I are represented by X, Y and Z. Substituents X, Y and Z may be H, $C_1$–$C_6$ alkyl, $C_1$–$C_6$ haloalkyl, hydroxy, $C_1$–$C_6$ alkoxy, $C_1$–$C_6$ haloalkoxy, phenyl, substituted phenyl, halo (F, Cl, Br, I), $C_1$–$C_6$ alkylthio, phenylthio, amino (including alkyl or phenyl substituted amino), carboxylic acids and esters. In addition, two adjacent substituents (i.e., X and Y or Y and Z) may be bonded together in a saturated cyclic structure. Examples of such cyclic structures could be represented by X and Y or Y and Z equal to —$(CH_2)_n$— where n=3, 4 or 5. These cyclic structures may also contain heteroatoms (e.g., N, O or S) as in the case where X and Y or Y and Z is equal to —$(CH_2)_nO$— where n=2 or 3.

Preferred compounds of the invention have the general formula:

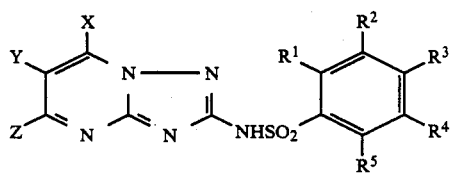

wherein $R^1$ represents halo (F, Cl, Br, I), —$NO_2$, phenyl, OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, halo (F, Cl, Br, I), $C_1$–$C_4$ alkyl, $COOR^7$ and —$OR^8$; $R^3$ is H; and $R^5$ represents H, $C_1$ to $C_4$ alkyl, halo (F, Cl, Br, I), $NO_2$, $CF_3$, —$OCF_3$, —$OCF_2CF_2H$, —$OCF_2CCl_2H$, —OCH₂CF₃, —SCF₃, —SCF₂CF₂H, —SCF₂CCl₂H, —SOCF₃, —SOCF₂CF₂H, —SOCF₂CCl₂H, —SO₂CF₃, —SO₂CF₂CF₂H, —SO₂CF₂CCl₂H, —SR⁶, —SOR⁶, —SO₂R⁶, —CN, —COOR⁷, —CONH₂, —CONHR⁸, —CONR⁸(R⁹), —SO₃R⁸, —SO₃CH₂CF₃, —CR⁶R⁶ OR⁶ and —CR⁶R⁶SR⁶ wherein Ar represents substituted or unsubstituted phenyl or substituted or unsubstituted heteroaryl (e.g., 2-pyridyl), R⁶ represents H, phenyl or C₁–C₄ alkyl, R⁷ represents C₁–C₆ alkyl, alkenyl, alkynyl, aryl, substituted alkyl or substituted phenyl and R⁸ and R⁹ individually represent C₁–C₄ alkyl; and X, Y and Z represent H, C₁–C₄ alkyl, C₁–C₄ alkoxy, halo, (F, Cl, Br, I), or X and Y or Y and Z can be bonded together to form a saturated cycloalkyl ring (i.e., —(CH₂)ₙ— wherein n is 3 or 4) or X and Y or Y and Z can be joined to form a ring containing a heteroatom (i.e., —O(CH₂)ₙ— wherein n is 2 or 3).

Preferred compounds of the invention also have the general formula:

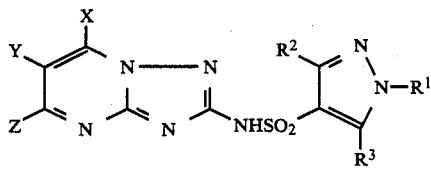

wherein R¹ represents H, C₁–C₄ alkyl or phenyl, R² and R³ represent independently H, C₁–C₄ alkyl, halo (F, Cl, Br, I), —NO₂, phenyl, —CF₃, benzyl, —COOR⁴, —CONH₂, —CONHR⁵, —CONR⁵R⁶, and CN wherein R⁴ represents C₁–C₆ alkyl, alkenyl, alkynyl, phenylalkyl, substituted alkyl or substituted phenyl, R⁵ and R⁶ individually represent C₁–C₄ alkyl; and X, Y and Z represent H, C₁–C₄ alkyl, C₁–C₄ alkoxy, halo (F, Cl, Br, I), or X and Y or Y and Z can be bonded together to form a saturated cycloalkyl ring (i.e., —(CH₂)ₙ— wherein n is 3 or 4) or X and Y or Y and Z can be bonded together to form a ring containing a heteroatom (i.e., —O(CH₂)ₙ— wherein n is 2 or 3).

Most preferred compounds of the invention have the general formula:

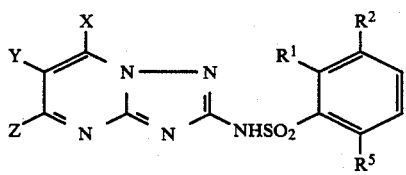

wherein R¹ represents C₁–C₄ alkyl, halo (F, Cl, Br, I), —NO₂, —SR⁶, —SOR⁶, SO₂R⁶, —COOR⁷ or CF₃; R² represents H, halo (F, Cl, Br, I), C₁–C₄ alkyl, and COOR⁷; and R⁵ represents H, C₁–C₄ alkyl, halo (F, Cl, Br, I), CH₂OR⁶, phenyl, NO₂ and COOR⁷ wherein R⁶ represents C₁–C₄ alkyl and R⁷ represents C₁–C₄ alkyl, C₁–C₄ alkenyl, C₁–C₄ alkynyl, 2-ethoxyethyl and 2-pyridylmethyl and X, Y and Z independently represent H, halo (F, Cl, Br, I), C₁–C₄ alkyl or C₁–C₄ alkoxy.

In addition certain derivatives of compounds corresponding to I also exhibit herbicidal activity. For example, compounds having the formula:

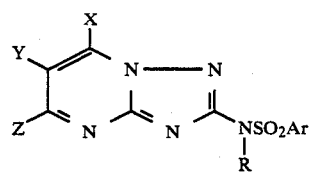

wherein Ar and X, Y and Z are as described above for compound I and R represents alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl, each containing from one to ten carbon atoms.

Preferred derivatives of the invention have the general formula:

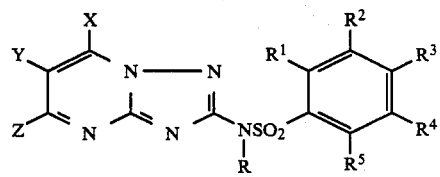

wherein X, Y, Z, R¹, R², R³, R⁴ and R⁵ are as described above for I and R represents C₁–C₄ alkyl, allyl, benzyl, —COR¹⁰, —CO₂R¹⁰, —CONR₂¹⁰, —COSR¹⁰, and —SO₂R¹⁰ wherein R¹⁰ is C₁–C₆ alkyl, phenyl, substituted phenyl or haloalkyl.

Most preferred derivatives of the invention have the general formula:

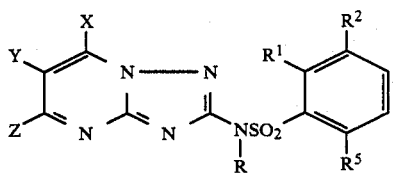

wherein X, Y, Z, R¹, R² and R⁵ are as described above for I and R is COR¹⁰ wherein R¹⁰ is C₁–C₄ alkyl.

Another series of derivatives of compounds of type I also possess herbicidal activity. These compounds are represented by the general formula:

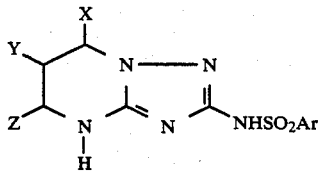

wherein X, Y, Z and Ar are as described above for compounds of type I.

Preferred derivatives of this invention have the general formula:

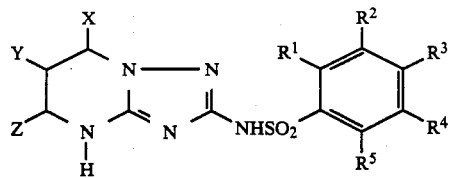

wherein X, Y, Z, R[1], R[2], R[3], R[4], and R[5] are as described above for I.

Most preferred derivatives of this invention have the general formula:

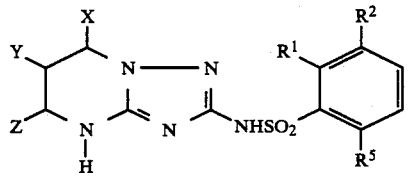

wherein X, Y, Z, R[1], R[2] and R[5] are as described above for I.

Furthermore, in the above invention corresponding to general formula III the existence of stereoisomerism is possible. For example stereoisomeric relationships exist when at least one of substituents X, Y and Z does not equal hydrogen. When only one of substituents X, Y and Z does not equal hydrogen the compound of type III may exist as a mixture of enantiomers. One enantiomer will be designated as having the R-configuration and the other will be designated as having the S-configuration. Each enantiomer may exhibit different levels of herbicidal activity. When two or more of substituents X, Y or Z in structure III do not equal hydrogen, the material may exist as a mixture of diastereomers. For example when two substituents among X, Y and Z do not equal hydrogen, the compound may exist as two diastereomers. When all three of substituents X, Y and Z do not equal hydrogen the compound may exist as four diastereomers. In addition all of the diastereomers described above may exist as a mixture of two enantiomers. All of the stereoisomers described above, diastereomers and their enantiomeric pairs, may exhibit diffent levels of herbicidal activity.

The synthesis of compounds of general structure I can be carried out in a straightforward manner as illustrated in SchemeI. Reaction of the appropriate aromatic sulfonyl chloride IV with the required 2-amino-1,2,4-triazolo[1,5-a]pyrimidine V under basic conditions yields the desired product I. A wide range of solvents may be employed (i.e., CH$_2$Cl$_2$, CH$_3$CN or pyridine) at temperatures ranging from 0° C. to reflux. Bases which serve as catalysts include pyridine, 4-dimethylaminopyridine and teritary alkylamines such as triethylamine or N-methylmorpholine. Generally the amino compound V serves as the limiting reagent. Molar ratios of between 1.1 and 1.0 for the sulfonylchloride to amino compound and molar ratios of between 5.0 and 1.1 for the base to amino compound are used most often. A wide range of concentrations may be employed (i.e., 0.1–5M). In addition it is sometimes advantageous to use a combination of pyridine derived base catalysts and tertiary amine bases. The useé of pyridine as a solvent is convenient as the pyridine can serve both as a solvent and catalyst in the transformation.

SCHEME I

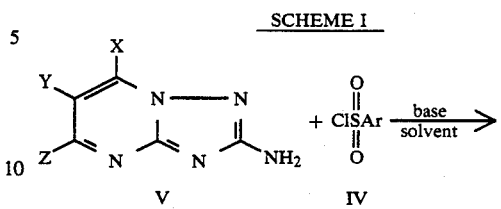

The required sulfonyl chlorides II are often commercially available. In some cases sulfonyl chlorides are prepared by the methodology outlined by H. T. Clarke et al., *Org. Synth.* Coll., Vol. 1, 2nd Ed., 1941, p. 85. This involves chlorosulfonation of the appropriate substituted benzene. Other sulfonyl chlorides can be prepared by methods described by R. V. Hoffman, *Org. Synth.*, Vol. 60, p. 121. This involves diazotization of the appropriate substituted aniline or amino substituted heterocycle with sodium nitrite in acidic media followed by reaction of the diazonium salt with sulfur dioxide in the presence of cuprous chloride. In addition certain sulfonyl chlorides can be prepared from aromatic compounds containing mercapto or benzylthio groups. The mercapto or benzylthio functional group is converted to a sulfonyl chloride by treatment with chloride in aqueous acidic media.

The required substituted 2-amino-1,2,4-triazolo[1,5-a]pyrimidine V can be prepared by methods outlind in "Heterocyclic Systems with Bridgehead Nitrogen Atoms", Part Two, W. L. Mosby, Interscience Publishers, 1961, p. 878. This involves the reaction of the appropriate 1,3-dicarbonyl compound with 3,5-diamino-1,2,4-triazole VI under acidic or basic conditions (Scheme II). The appropriate 1,3-dicarbonyl compounds include substituted 1,3-diketones, malonic ester, malonaldehyde, β-ketoesters, β-ketoaldehydes and α-formyl esters and derivatives thereof (i.e., acetals or enol ethers).

SCHEME II

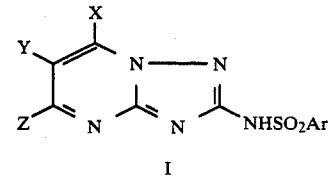

In instances where the 1,3-dicarbonyl compound is unsymmetrical, the possibility of obtaining two different isomers from condensation with VI exists. In general, under acidic conditions the exocyclic nitrogen in VI is the first to condense with the 1,3-dicarbonyl compound. Under basic conditions the endocyclic nitrogen in VI is more reactive. Consequently, in situations where a clear difference in reactivity of the two carbonyl functionalities in the 1,3-dicarbonyl compound exists, good to excellent measures of regiochemical control may be achieved by choice of reaction conditions.

In the synthetic routes listed above, compounds of type V where X and/or Z is OH are capable of undergoing further transformation (Scheme III). For example, treatment of compound V (X and/or Z=OH) with phosphorus oxychloride yields V (X and/or Z=Cl). The reaction is generally carried out at reflux in neat phosphorus oxychloride. Compound V (X and/or Z=Cl) can be further reacted with nucleophiles (i.e., NaOCH$_3$, MeMgBr) to yield V (X and/or Z OCH$_3$ or CH$_3$, respectively).

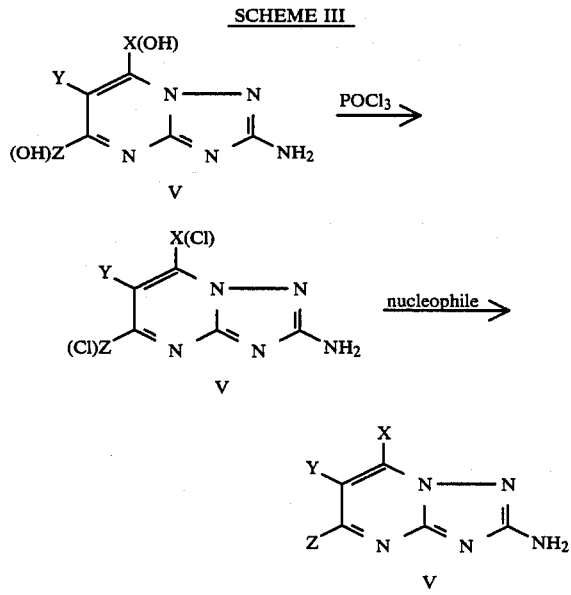

Compounds of the present invention represented by structure II are derived from compounds represented by structure I as illustrated in Scheme IV. The derivatization procedure involves treatment of compound I with a base in a suitable solvent followed by the introduction of an appropriate electrophilic derivatizing reagent. From this process compounds of general structure II can be isolated in good yields. Suitable bases include tertiary alkylamines (i.e., triethylamine), pyridine,4-dimethylaminopyridine, alkali metal carbonate (i.e., Na$_2$CO$_3$ or K$_2$CO$_3$) and alkali metal alkoxides (i.e., sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloro formates, aryl chloro formates, N,N-dialkyl carbamoyl chlorides, alkyl sulfonyl chlorides, aryl sulfonyl chlorides, alkyl chloro thioformates

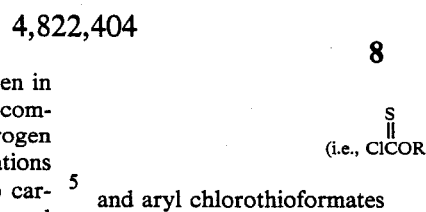

and aryl chlorothioformates

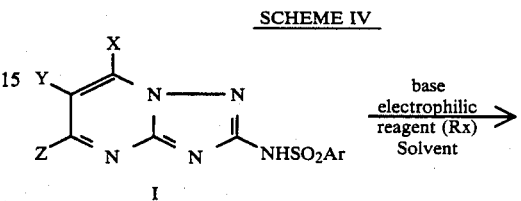

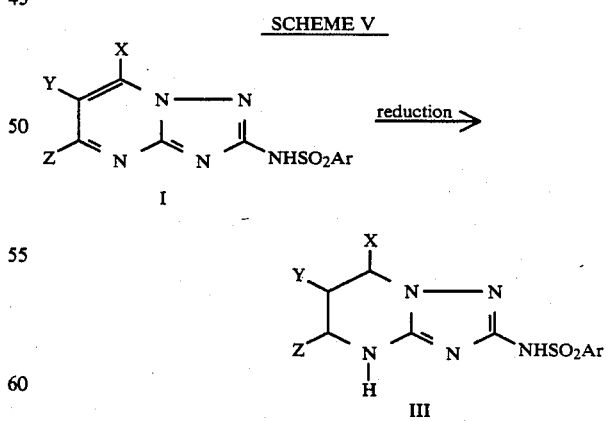

Compounds of the present invention represented by structure III are also derived from compounds represented by structure I as illustrated in Scheme V. The general process involves the reduction of compounds of general structure I with an appropriate reducing agent in a suitable solvent to yield compounds of general structure III. Reducing agents which are effective include metal hydrides (i.e., sodium borohydride) in the presence of acids (i.e., methane sulfonic acid) and hydrogen in the presence of normal hydrogenation catalysts (i.e., palladium on carbon). For reductions with metal hydrides polar aprotic solvents (i.e., DMSO) are most frequently used. For reductions using hydrogen and a catalyst, alcohols (i.e., ethanol) are most frequently employed as solvents.

A further procedure for the preparation of compounds of Formula I is illustrated in Scheme VI. In accordance with this process the sulfonamides VII are reacted with dimethyl N-cyanodithioiminocarbonate in the presence of a base in a solvent. Bases which are effective in this transformation include tertiary amines (i.e. triethylamine) or alkali metal hydroxides, alkoxides or carbonates (i.e. NaOH, NaOCH₃ or K₂CO₃). Appropriate solvents include acetone, methyl ethyl ketone, acetonitrile or tetrahydrofuran (THF). The reaction may be run at temperatures ranging from ambient temperature to reflux. The products of this transformation (VIII) may be isolated directly as their salts and converted to their neutral species by acidification. In some instances the salt may be used directly in subsequent transformations without isolation, purification or conversion to the corresponding neutral species. Compound VIII may be reacted with an excess of hydrazine to form the intermediate 1,2,4-triazoles IX. This reaction is generally carried out in solvents such as acetonitrile, THF, DMF, or DMSO at ambient temperature although higher temperatures may be employed to increase the rate of reaction. The amount of excess hydrazine utilized in this transformation ranges from 5 to 400 mole percent. The final step in this sequence for the conversion of compound IX to I may be carried out as generally outlined in "Heterocyclic Systems with Bridgehead Nitrogen Atoms", Part two, W. L. Mosby, Interscience Publishers, 1961, p. 878. A wide variety of 1,3-dicarbonyl compounds may be used in this reaction which may be run under acidic (i.e. acetic acid as a solvent), neutral (i.e. DMF as a solvent) or basic conditions (i.e. using alkali metal alkoxides or carbonates in polar aprotic solvents such as DMF or DMSO).

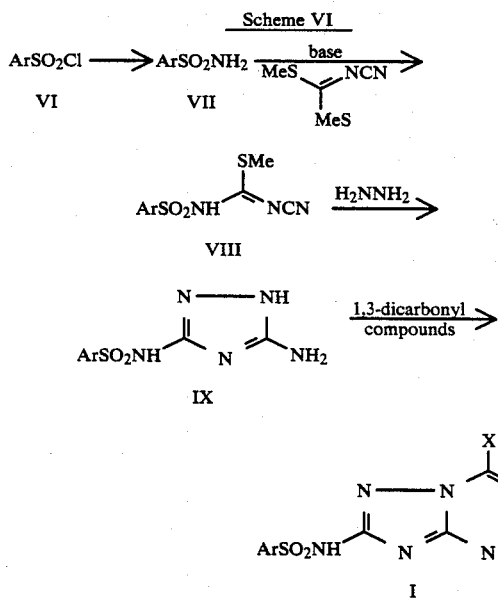

In examples where unsymmetrical 1,3-dicarbonyl compounds are employed in the process outlined in Scheme VI, the possibility of obtaining two different isomeric condensation products exists. Often the appropriate choice of reaction conditions (i.e. acidic or basic) allows for control of the regiochemistry of the annulation process.

In cases where β-ketoesters or malonic esters are used in the last step of the process described above, the products contain hydroxy groups (i.e. I where X and/or Z is OH). These products may be subjected to further transformations involving conversion of the hydroxy groups to chlorine with phosphorous oxychloride. The resulting halo substituted compounds are capable of undergoing reaction with nucleophiles to affect nucleophilic substitution of the halogen. This procedure is highly useful in th preparation of alkoxy, alkylthio and amino substituted heterocyclic ring systems.

An alternative procedure for the synthesis of intermediates of general structure VIII is illustrated in the following equation. The starting materials (X) may be prepared from aromatic sulfonamides by known art (i.e. F. L. Merchan, Synthesis, 984 (1982); R. Gompper, et al., Chem. Ber., 99, 2885, 2990 (1966)). These intermediates may be reacted with cyanamide in the presence of base to form VIII. Bases include tertiary amines and alkali metal alkoxides, hydroxides and carbonates. This reaction is most frequently carried out in acetonitrile or THF at temperatures ranging from ambient temperature to reflux.

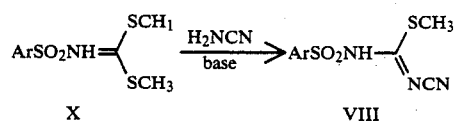

In certain instances intermediates X may convert to their corresponding mono or dichloro derivatives (i.e. XI and XII respectively). This may be accomplished by known art (i.e. E. Kuhle, et al., Angew, Chem Int. Ed. Engl., 6, 649 (1967)). These intermediates may then be advantageously used in a manner analogous to X in the synthesis of compounds of general structure I.

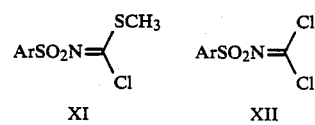

Using the routes illustrated above or minor variations based on the principles illustrated above the novel compounds of this invention can be prepared.

The invention is further illustrated by the following examples.

EXAMPLE 1A

2-Amino-5,7-dimethyl-1,2,4-triazolo(1,5-a)pyrimidine

A mixture of 49.5 g (0.500 mol) of 3,5-diamino-1,2,4-triazole, 100 g (1.00 mol) of 2,4-pentanedione, 400 g (1.00 mole) of 10 percent aqueous NaOH in 400 ml of EtOH was heated at reflux for 1.5 hours. After cooling to room temeprature the solid was collected by filtration and dried in vacuo to afford 45.0 g (55 percent) of pale yellow solid, m.p. >320° C.: IR (KBr) 3320, 3145, 1652, 1560 and 1535 cm⁻¹; 'H NMR (CF₃COOD) δ11.16 (2H, broad s, —NH₂), 7.42 (1H, s, aromatic H), 2.88 (3H, s, —CH₃) and 2.80 (3H, s, —CH₃).

Analysis: Calculated for C₇H₉N₅: C, 51.52; H, 5.56; N, 42.92. Found: C, 51.12; H, 5.44; N, 42.85.

EXAMPLE 1B

N-(5,7-Dimethyl-1,2,4-triazolo(1,5-a)pyrimidin-2-yl)-2-thiophene sulfonamide

A mixture of 4.24 g (26.0 mmol) of 2-amino-5,7-dimethyl-1,2,4-triazolo(1,5-a)pyrimidine, 5.08 g (27.8 mmol) of 2-thiophene sulfonyl chloride and 0.16 g (1.3 mmol) of 4-dimethylaminopyridine in 30 ml of dry pyridine was heated at reflux for 47 hours. The majority of the pyridine was removed by evaporation at reduced pressure and the residue was taken up in 1N NaOH, treated with charcoal and filtered through celite. The filtrated was treated with charcoal and filtered through celite. The yellow filtrate was cooled in an ice bath and acidified with concentrated HCl to precipitate a yellow solid. Drying in vacuo gave 0.50 g (6 percent) of the desired sulfonamide as a yellow powder, m.p. 236°–237.5° C.: IR (KBr) 3390 (broad), 1493, 1375 and 1156 cm$^{-1}$; $^1$H NMR (DMSO-d$_6$) δ12.3 (1H, broad, —SO$_2$NH—), 7.7–8.1 (2H, m, thiophene H's at 3- and 5-positions), 6.9–7.3 (2H, m including S at 7.03, thiophene H at 4-position and pyrimidine H), 2.62 (3H, s, —CH$_3$) and 2.49 (3H, s, —CH$_3$).

Analysis: Calculated for C$_{11}$H$_{11}$N$_5$O$_2$S$_2$: C, 42.71; H, 3.58; N, 22.64; S, 20.73. Found: C, 42.46; H, 3.39; N, 22.97; S, 20.48.

EXAMPLE 2

N-Acetyl-2,6-dichloro-N-(5,7-dimethyl-1,2,4-triazolo[1,5-a]-pyrimidin-2-yl)-benzenesulfonamide A solution of 0.50 g (1.3 mmol) of 2,6-dichloro-N-(5,7-dimethyl-1,2,4-triazolo[1,5-a]pyrimidin-2-yl)benzenesulfonamide, 2.12 ml (22.5 mmol) of acetic anhydride and 0.18 ml (1.3 mmol) of triethylamine in 4 ml of DMF was heated at 85° C. for 3 days. After cooling to room temperature, the product separated from solution and was collected by filtration and dried in vacuo to yield 0.20 g (39 percent) of the desired product as a solid, mp 219°–222° C. The product was characterized by IR and NMR spectroscopy.

Analysis: Calculated for C$_{15}$H$_{13}$Cl$_2$N$_5$O$_3$S: C, 43.49; H, 3.16; N, 16.91; Cl, 17.12; S, 7.74. Found: C, 43.79; H, 3.00; N, 17.03; Cl, 16.98; S, 7.99.

EXAMPLE 3

N'-Cyano-N-(2-nitrophenylsulfonyl)-2-methylisothiourea

A mixture of 2.02 g (10.0 mmol) of 2-nitrobenzenesulfonamide, 1.46 g (10.0 mmol) of dimethyl N-cyanodithioiminocarbonate and 1.38 g (10.0 mmol) of powdered, anydrous K$_2$CO$_3$ in 16 ml of acetone was heated at reflux for 20 hours. The reaction mixture was filtered and the solid collected was washed several times with acetone. The filtrate was evaporated and the orange oily residue was triturated with ether to afford a solid. The solid was collected by filtration, washed with ether and suspended in 10 ml of IN HCl. After stirring for 1 hour the solid was collected by filtration, washed with water and dried to yield 1.65 g (55 percent) of the desired product as a cream colored solid, mp 122° C. (decomposition). IR and $^1$H NMR spectra were consistent with the assigned structure.

Analysis: Calculated for C$_9$H$_8$N$_4$O$_4$S$_2$: C, 36.00; H, 2.69; N, 18.66; S, 21.35. Found: C, 36.10; H, 2.74; N, 18.72; S, 21.22.

EXAMPLE 4

N-(5-Amino-1,2,4-triazol-3-yl)-2-nitrobenzenesulfonamide

A suspension of 29.4 g (98.0 mmol) of N'-Cyano-N-(2-nitrophenylsulfnyl)-S-methylisothiourea in 100 ml of acetonitrile was treated with 6.2 ml (6.3 g, 0.20 mol) of anhydrous hydrazine. A mild exothermic reaction occurred as the reaction mixture became homogeneous. After stirring for 9 days the precipitated solid was collected by filtration and dried to afford 22.9 g of yellow solid. The crude product was recrystallized from HaAc to yield a total of 15.9 g (57 percent) of the desired product as a pale yellow solid, mp 255°–256° C. IR and $^1$H NMR spectra were consistent with the assigned structure.

Analysis: Calculated for C$_8$H$_8$N$_6$O$_4$S: C, 33.80; H, 2.84; N, 29.57; S, 11.28. Found: C, 34.11; H, 2.79; N, 29.35; S, 11.50.

EXAMPLE 5

N-(5,7-dimethyl-1,2,4-triazolo[1,5-a]pyrimidin-2-yl)-2-nitrobenzenesulfonamide

A mixture of 2.43 g (9.00 mmol) of N-(5-amino-1,2,4-triazol-3-yl)-2-nitrobenzenesulfonamide and 1.85 ml (1.80 g, 18.0 mmol) of 2,4 pentanedione in 25 ml of glacial acetic acid was heated at reflux for 19 hours. After cooling to room temperature, the solid which separated was collected by filtration, washed with acetic acid and dried in vacuo to yield 2.58 g (82 percent) of the desired product as an off-white crystalline solid, mp 255°–256° C. IR and $^1$H NMR spectra were in agreement with the assigned structure.

Analysis: Calculated for C$_{13}$H$_{12}$N$_6$O$_4$S: C, 44.83; H, 3.47; N, 24.13; S, 9.20. Found: C, 44.88; H, 3.34; N, 24.51; S, 9.09.

EXAMPLE 6

N'-Cyano-N-(2,5-dichlorophenylsulfonyl)-S-methylisothiourea

A solution of 10.6 g (43.2 mmol) of 2,5-dichlorobenzenesulfonamide, 7.15 g (44.0 mmol) of 90 percent dimethyl N-cyanodithioiminocarbonate and 1.8 g (44 mmol) of NaOH in 60 ml of ethanol and 10 ml of H$_2$O was heated at reflux for 6 hours. After cooling to room temperature the reaction mixture was poured into 600 ml of ice water. The resulting solution was acidified with 6N HCl to separate 2.2 g of the desired product as a white solid. Concentration of the filtrate gave an additional 8.5 g of the desired product. The total yield of material was 10.7 g (76 percent) of white solid, mp 145° C. IR and $^1$H NMR spectra were consistent with the assigned structure.

Analysis: Calculated for C$_9$H$_7$Cl$_2$N$_3$O$_2$S$_2$: C, 33.34; H, 2.18; N, 12.96. Found: C, 33.50; H, 2.39; N, 12.82.

EXAMPLE 7

N-(5-Amino-1,2,4-triazol-3-yl)-2,5-dichlorobenzenesulfonamide

A mixture of 8.51 g (26.2 mmol) of N'-cyano-N-(2,5-dichlorophenylsulfonyl)-S-methylisothiourea and 10 ml (10 g, 0.20 mol) of hydrazine monohydrate in 85 ml of ethanol was heated at reflux for 30 minutes. After cooling to room temperature, the solid which separated was collected and suspended in 170 ml of H$_2$O and the suspension was acidified with concentrated aqueous HCl. After stirring the suspension for 4 hours the solid was collected and dried in vacuo to yield 5.10 g (57 percent) of the desired product as a hydrochloride salt, mp 306°–308° C. IR and $^1$H NMR spectra were consistent with the assigned structure.

Analysis: Calculated for C$_8$H$_7$Cl$_2$N$_5$O$_2$S.HCl: C, 27.88; H, 2.34; N, 20.32. Found: C, 28.36; H, 2.50; N, 19.78.

EXAMPLE 8

N-(5,7-dimethyl-1,2,4-triazolo[1,5-a]pyrimidin-2-yl)-2,5-dichlorobenzene-sulfonamide A solution of 4.60 g (13.3 mmol) of N-(5-amino-1,2,4-triazol-3-yl)-2,5-dichlorobenzenesulfonamide hydrochloride and 4.0 g (40 mmol) of 2,4-pentanedione in 60 ml of glacial acetic acid was heated at reflux for 4 hours. The reaction mixture was cooled to room temperature and poured into 500 ml of ice water to separate a solid. The solid was collected by filtration and dried to yield 4.53 g (92 percent) of the desired product as a white solid, mp 216.5°–218.5° C.

Analysis: Calculated for $C_{13}H_{11}Cl_2N_5O_2S$: C, 41.95; H, 2.98; N, 18.81. Found: C, 41.83; H, 3.10; N, 18.67.

EXAMPLE 9

2-Chloro-N-(5-methyl-7-trifluoromethyl-1,2,4-triazolo[1,5-a]pyrimidin-2-yl)benzenesulfonamide A mixture of 2.19 g (8.00 mmol) of N-(5-amino-1,2,4-triazol-3-yl)-2-chlorobenzenesulfonamide and 1.09 ml (1.38 g, 8.96 mmol) of 1,1,1-trifluoro-2,4-pentanedione in 9 ml of glacial acetic acid was heated at reflux for 21 hours. After cooling to room temperature, the reaction mixture was poured into a mixture of ice and water. The solid which separated was collected by filtration, washed with water and dried to yield 2.90 g (93 percent) of the desired product as a white solid, mp 203°–204.5° C. IR and $^1$H NMR spectra were in agreement with the assigned structure.

Analysis: Calculated for $C_{13}H_9ClF_3N_5O_2S$: C, 39.86; H, 2.32; H, 17.88; Cl, 9.05; S, 8.18. Found: C, 40.23; H, 2.31; N, 18.22; Cl, 9.13; S, 8.26.

EXAMPLE 10

2-Chloro-N-(7-methyl-1,2,4-triazolo[1,5-a]pyrimidin-2-yl)benzenesulfonamide

A sample of 3.0 ml (2.7 g, 20 mmol) of acetylacetaldehyde dimethylacetal was added to a solution of 2.74 g (10.0 mmol) of N-(5-amino-1,2,4-triazol-3-yl)-2-chlorobenzenesulfonamide in 20 ml of glacial acetic acid at reflux over 12 hours. After the addition was complete the reaction mixture was heated at reflux for 15 hours and cooled to room temperature. The solid which separated was collected by filtration, washed with acetic acid and dried to yield 1.92 g (59 percent) of the desired product as white solid, mp 267.5°–269° C. IR and $^1$H NMR spectra were in agreement with the assigned structure.

Analysis: Calculated for $C_{12}H_{10}ClN_5O_2S$: C, 44.52; H, 3.11; N, 21.63; Cl, 10.95; S, 9.90. Found: C, 44.36; H, 3.07; N, 21.69; Cl, 10.82; S, 10.15.

EXAMPLE 11

2-Chloro-N-(1,2,4-triazolo[1,5-a]pyrimidin-2-yl)benzenesulfonamide

A mixture of 2.74 g (10.0 mmol) of N-(5-amino-1,2,4-triazol-3-yl)-2-chlorobenzenesulfonamide and 3.3 ml (3.3 g, 20 mmol) of malonaldehyde bis(dimethylacetal) in 10 ml of glacial acetic acid was heated at reflux for 24 hours. After cooling to room temperature, the solid which separated was collected by filtration, washed with acetic acid and dried to yield 1.78 g (58 percent) of the desired product as tan solid, mp 253.5°–256.5° C. IR and $^1$H NMR spectra were in agreement with the assigned structure.

Analysis: Calculated for $C_{11}H_8ClN_5O_2S$: C, 42.66; H, 2.60; N, 22.61; Cl, 11.45; S, 10.35. Found: C, 42.97; H, 2.60; N, 22.42; Cl, 11.19; S, 10.07.

EXAMPLE 12

2-Chloro-N-(6-Chloro-1,2,4-triazolo[1,5-a]pyrimidin-2-yl)benzenesulfonamide

A mixture of 2.46 g (9.00 mmol) of N-(5-amino-1,2,4-triazol-3-yl)-2-chlorobenzenesulfonamide and 1.67 g (9.90 mmol) of mucochloric acid in 20 ml of DMF was heated to reflux for 16.5 hours. After cooling to room temperature, the solvent was removed by evaporation at reduced pressure and the residue was treated with 20 ml of 0.5N NaOH. After stirring vigorously for ~30 minutes the mixture was filtered through celite and the filtrate was acidified with 2N HCl. The solid which separated was collected by filtration, washed with water and recrystallized from acetic acid—water to yield 0.70 g (23 percent) of the desired product as a light brown solid, mp 285.5°–260.5° C. IR and $^1$H NMR spectra were in agreement with the assigned structure.

Analysis: Calculated for $C_{11}H_7Cl_2N_5O_2S$: C, 38.39; H, 2.05; N, 20.35; Cl, 20.60; S, 9.32. Found: C, 38.74; H, 2.08; N, 20.84; Cl, 19.54; S, 8.70.

EXAMPLE 13

2-Chloro-N-(6-methyl-1,2,4-triazolo[1,5-a]pyrimidin-2-yl)benzenesulfonamide

A mixture of 2.0 g (8.36 mmol) of 1,3-bis(dimethylamino)-2-methyltrimethinium perchlorate and 2.29 g (8.36 mmol) of N-(5-amino-1,2,4-triazol-3-yl)-2-chlorobenzenesulfonamide in 25 ml of glacial acetic acid was heated at reflux for 19 hours. The solvent was removed by evaporation at reduced pressure, and the residue was treated with 20 ml of 0.5N NaOH. Some additional $^1$N NaOH was added to dissolve all of the material (~pH 10). The solution was filtered and the filtrate was acidified with 2N HCl to precipitate a solid. The solid was collected by filtration, washed with water and dried to yield 2.34 g (87 percent) of the desired product as a pale yellow solid, mp 236°–239° C. IR and $^1$H NMR spectra were in agreement with the assigned structure.

Analysis: Calculated for $C_{12}H_{10}ClN_5O_2S$: C, 44.52; H, 3.11; N, 21.63; Cl, 10.95; S, 9.90. Found: C, 44.17; H, 3.05; N, 21.93; Cl, 11.01; S, 9.69.

EXAMPLE 14

N-(5-Amino-1,2,4-triazol-3-yl)-2,6-dichlorobenzenesulfonamide

A mixture of 90.1 g (0.398 mol) of 2,6-dichlorobenzenesulfonamide, 64.7 g (0.398 mol) of dimethyl N-cyanodithioiminocarbonate and 58.3 g (0.420 mol) of powdered anhydrous $K_2CO_3$ in 800 ml of THF was heated at reflux for 3 hours. After cooling to 30° C., 25.3 ml (25.6 g, 0.798 mol) of anhydrous hydrazine was added dropwise over 30 minutes. The resulting mixture was stirred for 3 days at ambient temperature and filtered. The solid collected was washed with THF, suspended in 400 ml of water and acidified with 180 ml of acetic acid. The resulting mixture was filtered, and the solid collected was washed with water and dried to yield 112 g (91 percent) of the desired product as a white solid, mp 300° C. (decomp.) IR and $^1$H NMR spectra were in agreement with the assigned structure.

Analysis: Calculated for $C_8H_7Cl_2N_5O_2S$: C, 31.18; H, 2.29; N, 22.73; Cl, 23.01; S, 10.40. Found: C, 31.39; H, 2.26; N, 22.70; Cl, 22.88; S, 10.25.

The compounds prepared employing the above general procedures and the appropriate starting materials are listed in the following Tables I through XV.

TABLE I

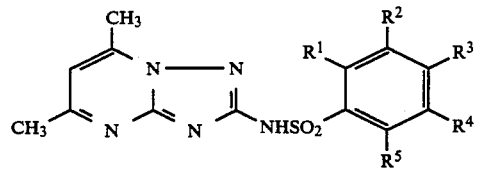

| Compound | $R^1$ | $R^2$ | $R^3$ | $R^4$ | $R^5$ | Melting Point | Analysis | C | H | N | Cl | S |
|---|---|---|---|---|---|---|---|---|---|---|---|---|
| 1 | H | H | H | H | H | 228°–229.5° C. | Calcd. for $C_{13}H_{13}N_5O_2S$: | 51.47 | 4.32 | 23.09 | | 10.57 |
| | | | | | | | Found: | 51.40 | 4.13 | 23.00 | | 10.44 |
| 2 | H | H | $CH_3$ | H | H | 238°–239° C. | Calcd. for $C_{14}H_{15}N_5O_2S$: | 52.98 | 4.76 | 22.07 | | |
| | | | | | | | Found: | 52.28 | 4.64 | 21.80 | | |
| 3 | $CF_3$ | H | H | H | H | 246.5°–248° C. | Calcd. for $C_{14}H_{12}F_3N_5O_2S$: | 45.28 | 3.26 | 18.86 | | 8.63 |
| | | | | | | | Found: | 45.31 | 3.33 | 18.74 | | 8.71 |
| 4 | $CH_3$ | H | H | H | H | 202.5°–203.5° C. | Calcd. for $C_{14}H_{15}N_5O_2S$: | 52.98 | 4.76 | 22.07 | | 10.10 |
| | | | | | | | Found: | 52.43 | 4.56 | 21.78 | | 9.59 |
| 5 | $NO_2$ | H | H | H | H | 255°–256° C. (decomp.) | Calcd. for $C_{13}H_{12}N_6O_4S$: | 44.83 | 3.47 | 24.13 | | 9.20 |
| | | | | | | | Found: | 44.88 | 3.34 | 24.51 | | 9.09 |
| 6 | Cl | H | H | H | H | 216.5°–219.5° C. | Calcd. for $C_{13}H_{12}ClN_5O_2S$: | 46.23 | 3.58 | 20.73 | 10.50 | 9.49 |
| | | | | | | | Found: | 45.97 | 3.66 | 21.01 | 10.73 | 9.30 |
| 7 | H | H | Cl | H | H | 254°–255.5° C. | Calcd. for $C_{13}H_{12}ClN_5O_2S$: | 46.22 | 3.58 | 20.73 | | |
| | | | | | | | Found: | 46.10 | 3.75 | 20.69 | | |
| 8 | H | H | $OCH_3$ | H | H | 198.5°–199.5° C. | Calcd. for $C_{14}H_{15}N_5O_3S$: | 50.44 | 4.54 | 21.01 | | |
| | | | | | | | Found: | 50.43 | 4.70 | 20.99 | | |
| 9 | i-Pr | H | i-Pr | H | i-Pr | 283° C. (decomp.) | Calcd. for $C_{22}H_{31}N_5O_2S$: | 61.51 | 7.27 | 16.30 | | |
| | | | | | | | Found: | 61.30 | 7.33 | 16.28 | | |
| 10 | Cl | H | H | H | Cl | 259°–261° C. | Calcd. for $C_{13}H_{11}Cl_2N_5O_2S$: | 41.95 | 2.98 | 18.81 | 19.05 | 8.61 |
| | | | | | | | Found: | 41.86 | 2.94 | 19.09 | 18.92 | 8.39 |
| 11 | F | H | H | H | F | 261°–262° C. | Calcd. for $C_{13}H_{11}F_2N_5O_2S$: | 46.02 | 3.27 | 20.64 | | |
| | | | | | | | Found: | 45.94 | 3.19 | 20.79 | | |
| 12 | Cl | Cl | H | H | H | 231°–233° C. | Calcd. for $C_{11}H_7Cl_2N_5O_2S$: | 41.95 | 2.98 | 18.81 | | |
| | | | | | | | Found: | 41.83 | 2.90 | 19.55 | | |
| 13 | Cl | H | H | Cl | H | 216.5°–218.5° C. | Calcd. for $C_{13}H_{11}Cl_2N_5O_2S$: | 41.95 | 2.98 | 18.81 | | |
| | | | | | | | Found: | 41.83 | 3.10 | 18.67 | | |
| 14 | Cl | H | Cl | H | H | 244.5°–245.5° C. | Calcd. for $C_{13}H_{11}Cl_2N_5O_2S$: | 41.94 | 2.98 | 18.81 | | |
| | | | | | | | Found: | 41.90 | 2.96 | 19.61 | | |
| 15 | H | Cl | H | Cl | H | 207°–208° C. | Calcd. for $C_{13}H_{11}Cl_2N_5O_2S$: | 41.94 | 2.98 | 18.81 | 19.05 | 8.61 |
| | | | | | | | Found: | 41.94 | 2.86 | 18.84 | 18.89 | 8.59 |
| 16 | Cl | $CH_3$ | H | H | Cl | 249°–251° C. | Calcd. for $C_{14}H_{13}Cl_2N_5O_2S$: | 43.53 | 3.39 | 18.13 | 18.36 | 8.30 |
| | | | | | | | Found: | 43.39 | 3.42 | 18.57 | 18.28 | 8.23 |
| 17 | $NO_2$ | H | H | H | $CH_3$ | 244°–246° C. (decomp.) | Calcd. for $C_{14}H_{14}N_6O_4S$: | 46.40 | 3.89 | 23.19 | | |
| | | | | | | | Found: | 46.22 | 2.82 | 23.05 | | |
| 18 | H | Cl | Cl | H | H | 218°–220° C. | Calcd. for $C_{13}H_{11}Cl_2N_5O_2S$: | 41.94 | 2.98 | 18.81 | 19.05 | 8.61 |
| | | | | | | | Found: | 41.87 | 2.97 | 18.75 | 19.01 | 8.74 |
| 19 | H | Cl | H | H | H | 227.5°–228° C. | Calcd. for $C_{13}H_{12}ClN_5O_2S$: | 46.23 | 3.58 | 20.73 | | |
| | | | | | | | Found: | 46.38 | 3.65 | 20.81 | | |
| 20 | H | H | $NO_2$ | H | H | 251°–252° C. | Calcd. for $C_{13}H_{12}N_6O_4S$: | 44.83 | 3.47 | 24.13 | | |
| | | | | | | | Found: | 44.55 | 3.41 | 24.32 | | |
| 21 | H | $CH_3$ | H | H | H | 208°–209.5° C. | Calcd. for $C_{14}H_{15}N_5O_2S$: | 52.98 | 4.76 | 22.07 | | |
| | | | | | | | Found: | 52.73 | 4.73 | 21.80 | | |
| 22 | H | $NO_2$ | H | H | H | 246°–250° C. (decomp.) | Calcd. for $C_{13}H_{12}N_6O_4S$ | 44.83 | 3.47 | 24.13 | | |
| | | | | | | | Found: | 45.00 | 3.56 | 23.82 | | |

TABLE II

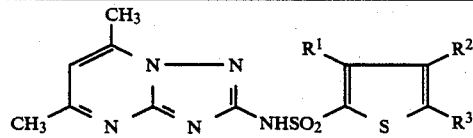

| Compound | $R^1$ | $R^2$ | $R^3$ | Melting Point | Analysis | C | H | N | Cl | Br | S |
|---|---|---|---|---|---|---|---|---|---|---|---|
| 23 | H | H | H | 236°–237.5° C. | Calcd. for $C_{11}H_{11}N_5O_2S_2$: | 42.71 | 3.58 | 22.64 | | | 20.73 |
| | | | | | Found: | 42.46 | 3.39 | 22.97 | | | 20.48 |
| 24 | H | H | Cl | 200°–202° C. | Calcd. for $C_{11}H_{10}ClN_5O_2S_2$: | 38.43 | 2.93 | 20.37 | 10.31 | | 18.65 |
| | | | | | Found: | 38.08 | 2.83 | 20.47 | 8.59 | | 18.91 |
| 25 | H | Br | Br | 183°–185° C. | Calcd. for $C_{11}H_9Br_2N_5O_2S_2$: | 28.28 | 1.94 | 14.99 | | 34.21 | 13.73 |
| | | | | | Found: | 28.06 | 1.78 | 14.97 | | 33.60 | 13.90 |

TABLE III

Structure: 3,5-dimethyl-4-methyl-pyrimidinyl-N-N-triazine-NHSO$_2$-phenyl(R$^1$-R$^5$)

| Compound | R$^1$ | R$^2$ | R$^3$ | R$^4$ | R$^5$ | Melting Point | Analysis | C | H | N | Cl | S |
|---|---|---|---|---|---|---|---|---|---|---|---|---|
| 26 | Cl | H | H | H | H | 273°–280° C. | Calcd. for C$_{14}$H$_{14}$ClN$_5$O$_2$S: | 47.80 | 4.01 | 19.91 | 10.08 | 9.11 |
|   |   |   |   |   |   |   | Found: | 47.78 | 3.90 | 20.19 | 10.20 | 9.17 |
| 27 | Cl | H | H | H | Cl | 347° C. | Calcd. for C$_{14}$H$_{13}$Cl$_2$N$_5$O$_2$S: | 43.53 | 3.39 | 18.13 | 18.35 | 8.30 |
|   |   |   |   |   |   |   | Found: | 43.52 | 3.29 | 18.42 | 18.37 | 8.29 |

TABLE IV

| Compound | R$^1$ | R$^2$ | R$^3$ | R$^4$ | R$^5$ | Melting Point | Analysis | C | H | N | Cl | S |
|---|---|---|---|---|---|---|---|---|---|---|---|---|
| 28 | Cl | H | H | H | H | 266°–269° C. | Calcd. for C$_{13}$H$_{11}$Cl$_2$N$_5$O$_2$S: | 41.95 | 2.98 | 18.81 | 19.05 | 8.61 |
|   |   |   |   |   |   |   | Found: | 42.51 | 3.03 | 18.98 | 18.16 | 8.41 |
| 29 | Cl | H | H | H | Cl | 296°–297° C. | Calcd. for C$_{13}$H$_{10}$Cl$_2$N$_5$O$_2$S: | 38.39 | 2.48 | 17.22 |   |   |
|   |   |   |   |   |   |   | Found: | 38.48 | 2.44 | 17.58 |   |   |

TABLE V

| Compound | R$^1$ | R$^2$ | R$^3$ | R$^4$ | R$^5$ | Melting Point | Analysis | C | H | N | Cl | S |
|---|---|---|---|---|---|---|---|---|---|---|---|---|
| 30 | Cl | H | H | H | H | 224°–226° C. | Calcd. for C$_{13}$H$_6$ClF$_6$N$_5$O$_2$S: | 35.02 | 1.36 | 15.71 | 7.95 | 7.19 |
|   |   |   |   |   |   |   | Found: | 35.31 | 1.38 | 15.95 | 7.72 | 7.40 |
| 31 | Cl | H | H | H | Cl | 238°–240° C. | Calcd. for C$_{13}$H$_5$Cl$_2$F$_6$N$_5$O$_2$S: | 32.51 | 2.05 | 20.35 | 14.77 | 6.68 |
|   |   |   |   |   |   |   | Found: | 32.19 | 1.01 | 14.57 | 14.51 | 6.86 |

TABLE VI

| Compound | R$^1$ | R$^2$ | R$^3$ | R$^4$ | R$^5$ | Melting Point | Analysis | C | H | N | Cl | S |
|---|---|---|---|---|---|---|---|---|---|---|---|---|
| 32 | Cl | H | H | H | H | 216°–218° C. | Calcd. for C$_{15}$H$_{16}$ClN$_5$O$_2$S: | 49.25 | 4.41 | 19.14 | 9.69 | 8.76 |
|   |   |   |   |   |   |   | Found: | 49.18 | 4.36 | 19.45 | 9.64 | 8.75 |
| 33 | Cl | H | H | H | Cl | 259°–261° C. | Calcd. for C$_{15}$H$_{15}$Cl$_2$N$_5$O$_2$S: | 45.01 | 3.78 | 17.50 | 17.72 | 8.01 |
|   |   |   |   |   |   |   | Found: | 44.44 | 3.72 | 17.79 | 17.33 | 8.32 |

TABLE VII

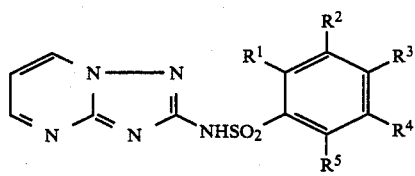

| Compound | R¹ | R² | R³ | R⁴ | R⁵ | Melting Point | Analysis | C | H | N | Cl | S |
|---|---|---|---|---|---|---|---|---|---|---|---|---|
| 34 | Cl | H | H | H | H | 253.5°–256.5° C. | Calcd. for $C_{11}H_8ClN_5O_2S$: | 42.66 | 2.60 | 22.61 | 11.45 | 10.35 |
|  |  |  |  |  |  |  | Found: | 42.97 | 2.60 | 22.42 | 11.19 | 10.07 |
| 35 | Cl | H | H | H | Cl | 264°–269° C. | Calcd. for $C_{11}H_7Cl_2N_5O_2S$: | 38.38 | 2.05 | 20.35 | 20.61 | 9.32 |
|  |  |  |  |  |  |  | Found: | 38.29 | 2.05 | 20.08 | 19.80 | 9.13 |

TABLE VIII

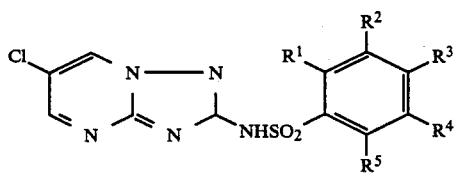

| Compound | R¹ | R² | R³ | R⁴ | R⁵ | Melting Point | Analysis | C | H | N | Cl | S |
|---|---|---|---|---|---|---|---|---|---|---|---|---|
| 36 | Cl | H | H | H | H | 258.5°–260.5° C. | Calcd. for $C_{11}H_7Cl_2N_5O_2S$: | 38.39 | 2.05 | 20.35 | 20.60 | 9.32 |
|  |  |  |  |  |  |  | Found: | 38.74 | 2.08 | 20.84 | 19.54 | 8.70 |
| 37 | Cl | H | H | H | Cl | 262°–264° C. | Calcd. for $C_{11}H_6Cl_3N_5O_2S$: | 34.89 | 1.60 | 18.50 |  |  |
|  |  |  |  |  |  |  | Found: | 34.72 | 1.78 | 19.12 |  |  |

TABLE IX

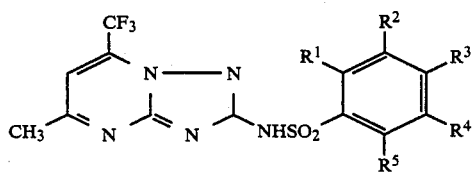

| Compound | R¹ | R² | R³ | R⁴ | R⁵ | Melting Point | Analysis | C | H | N | Cl | S |
|---|---|---|---|---|---|---|---|---|---|---|---|---|
| 38 | Cl | H | H | H | H | 203°–204.5° C. | Calcd. for $C_{13}H_9ClF_3N_5O_2S$: | 39.86 | 2.32 | 17.88 | 9.05 | 8.18 |
|  |  |  |  |  |  |  | Found: | 40.23 | 2.31 | 18.22 | 9.13 | 8.26 |
| 39 | Cl | H | H | H | Cl |  | Calcd. for $C_{13}H_8Cl_2F_3N_5O_2S$: | 36.63 | 1.89 | 16.43 |  |  |
|  |  |  |  |  |  |  | Found: | 36.57 | 1.81 | 17.00 |  |  |

TABLE X

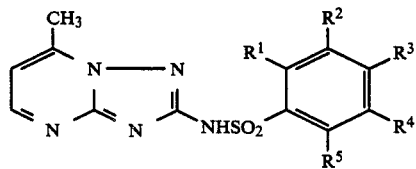

| Compound | R¹ | R² | R³ | R⁴ | R⁵ | Melting Point | Analysis | C | H | N | Cl | S |
|---|---|---|---|---|---|---|---|---|---|---|---|---|
| 40 | Cl | H | H | H | H | 267.5°–269° C. | Calcd. for $C_{12}H_{10}ClN_5O_2S$: | 44.52 | 3.11 | 21.63 | 10.95 | 9.90 |
|  |  |  |  |  |  |  | Found: | 44.36 | 3.07 | 21.69 | 10.82 | 10.15 |

TABLE XI

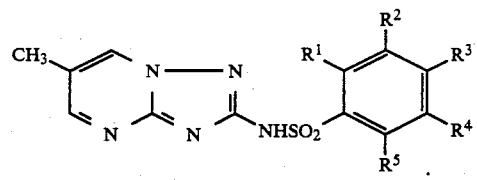

| Compound | R¹ | R² | R³ | R⁴ | R⁵ | Melting Point | Analysis | C | H | N | Cl | S |
|---|---|---|---|---|---|---|---|---|---|---|---|---|
| 41 | Cl | H | H | H | H | 236°–239° C. | Calcd. for $C_{12}H_{10}ClN_5O_2S$: | 44.52 | 3.11 | 21.63 | 10.95 | 9.90 |
|  |  |  |  |  |  |  | Found: | 44.17 | 3.05 | 21.93 | 11.01 | 9.69 |

TABLE XII

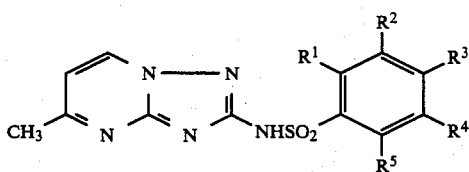

| Compound | R¹ | R² | R³ | R⁴ | R⁵ | Melting Point | Analysis | C | H | N |
|---|---|---|---|---|---|---|---|---|---|---|
| 42 | Cl | H | H | H | Cl | 305°–310° C. (decomp.) | Calcd. for $C_{12}H_9Cl_2N_5O_2S$: | 40.23 | 2.53 | 19.55 |
|  |  |  |  |  |  |  | Found: | 40.31 | 2.57 | 20.88 |

TABLE XIII

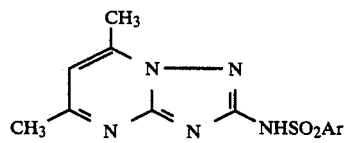

| Compound | Ar | Melting Point | Analysis | C | H | N | S |
|---|---|---|---|---|---|---|---|
| 43 | 1-napthyl | 221–224° C. | Calcd. for $C_{17}H_{15}N_5O_2S$: | 57.78 | 4.28 | 19.82 | 9.07 |
|  |  |  | Found: | 58.15 | 4.18 | 19.69 | 9.23 |
| 44 | 2-napthyl | 242–245° C. | Calcd. for $C_{17}H_{15}N_5O_2S$: | 57.78 | 4.28 | 19.82 | 9.07 |
|  |  |  | Found: | 57.36 | 4.29 | 20.27 | 9.40 |

TABLE XIV

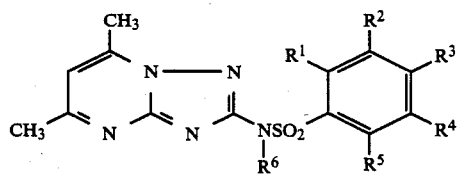

| Compound | R¹ | R² | R³ | R⁴ | R⁵ | R⁶ | Melting Point | Analysis | C | H | N | Cl | S |
|---|---|---|---|---|---|---|---|---|---|---|---|---|---|
| 45 | Cl | H | H | H | H | CH₂Ph | 240°–242° C. | Calcd. for $C_{20}H_{18}ClN_5O_2S$: | 56.14 | 4.24 | 16.37 | 8.29 | 7.49 |
|  |  |  |  |  |  |  |  | Found: | 55.62 | 4.08 | 16.52 | 9.51 | 6.72 |
| 46 | H | H | CH₃ | H | H | CH₂Ph | 137°–138° C. | Calcd. for $C_{21}H_{21}N_5O_2S$: | 61.90 | 5.19 | 17.18 |  | 7.85 |
|  |  |  |  |  |  |  |  | Found: | 61.84 | 5.07 | 17.19 |  | 7.78 |
| 47 | Cl | H | H | H | Cl | COCH₃ | 219°–222° C. | Calcd. for $C_{15}H_{13}Cl_2N_5O_3S$: | 43.49 | 3.16 | 16.91 | 17.12 | 7.74 |
|  |  |  |  |  |  |  |  | Found: | 43.79 | 3.00 | 17.03 | 16.98 | 7.99 |

TABLE XV

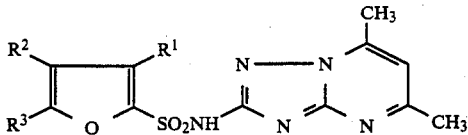

| Compound | R¹ | R² | R³ | Melting Point | Elemental Composition Analysis | C | H | N |
|---|---|---|---|---|---|---|---|---|
| 48 | H | H | H | 216–218° C. | Calcd. for $C_{11}H_{11}N_5O_3S$: | 45.04 | 3.78 | 23.88 |
|  |  |  |  |  | Found: | 45.10 | 3.65 | 23.69 |

The compounds of the present invention are highly effective herbicides. They have utility for broadspectrum pre- and/or postemergence weed control in areas where complete vegetation control is desired. The subject compounds are also useful for selective pre- and/or postemergence weed control in crops such as wheat. Certain of these compounds are effective for the control of nutsedge (Cyperus spp.) and some compounds may be used for selective weed control in corn, soybeans and rice.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-to-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, akyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acid, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic 61 (molecular weight about 1000), polyethylene glycol ester of tall oil acids, sodium octophenoxyethoxyethyl sulfate, tris(polyoxyethylene)-sorbitan monostearate (Tween 60), and sodium dihexylsulfosuccinate.

Other adjuvants, such as, for example, crop oil and crop oil concentrates, may also be included in the formulated compositions of the invention as is known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15-50 weight percent. The active ingredient compositions can also contain other compatible additaments, for example, phytotoxicants, plant growth regulators, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1-methylurea (Lorox®) and 1,1-dimethyl-3-(α,α,α-trifluoro-m-tolyl)urea (Cotoran®); the triazines such as 2-chloro-4-(ethylamino)-6-(isopropylamino)-s-triazine and 2-chloro-4-(1-cyano-1-methylethylamino)-6-ethylamino-s-triazine (Bladex®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon®) and 3,6-dichloropicolinic acid (Lontrel®); 4-chloro-2-butynyl-3-chlorophenyl carbamate (Carbyne®); diisopropylthiocarbamic acid, ester with 2,3-dichloroallyl alcohol (Avadex®); diisopropylthiocarbamic acid, ester with 2,3,3-trichloroallyl alcohol (Avadex® BVD); ethyl-N-benzoyl-N-(3,4-dichlorophenyl)-2-aminopropionate (Suffix®); 1,2-dimethyl-3,5-diphenyl-pyrazolium methylsulfate (Avenge®); methyl (2-[4-(2,4-dichlorophenoxy)phenoxy]propanoate) (Hoelon®); butyl 2-[4-[(5-(trifluoromethyl)-2-pyridinyl)oxy]phenoxy]propanoate (Fusilade®); esters of 2-[4-[(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone®); 3-isopropyl-1H-2,1,3-benzothiadiazin-(4)-3H-one 2,2-dioxide; α,α,α-trifluoro-2,6-dinitro-N,N,-dipropyl-p-toluidine; 1,1'-dimethyl-4,4'-bipyridinium ion; 2-chloro-2',6'-diethyl-(methoxymethyl)acetanilide; and 2-[1-(ethoxyimino)-butyl]-5-[(2-ethylthio)propyl]-3-hydroxy-2-cyclohexen-1-one (Poast®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equaly effective at similar concentrations or against the same plant species. In non-selective preemergence and foliar treatments, the active ingredients of the invention are usually applied at an approximate rate of from about 0.1 to about 10 pounds/acre. In pre- and postemergence operations for selective uses, a dosage of about 0.01 to about 10 pounds/acre is generally applicable, a rate of 0.01 to 4 pounds/acre being preferred.

Plant species in the following tests were the following:

| | Common Name | Scientific Name |
|---|---|---|
| A. | cotton | Gossypium spp. |
| B. | rape | Brassica napus |
| C. | soybean | Glycine max |
| D. | sugar beet | Beta vulgaris |
| E. | cocklebur | Xanthium spp. |
| F. | jimsonweed | Datura stramonium |
| G. | annual morning glory | Ipomoea spp. |
| H. | pigweed | Amaranthus spp. |
| I. | velvetleaf | Abutilon theophrasti |
| J. | corn | Zea mays |
| K. | rice | Oryza sativa |
| L. | sorghum | Sorghum vulgare |
| M. | wheat | Triticum aestivum |
| N. | barnyardgrass (watergrass) | Echinochloa crusgalli |
| O. | crabgrass | Digitaria spp. |
| P. | yellow foxtail | Setaria lutescens |
| Q. | johnson grass | Sorghum halepense |
| R. | wild oats | Avena fatua |
| S. | yellow nutsedge | Cyperus esculentus |

EXAMPLE 15

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–14 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species.

TABLE XVI

POSTEMERGENT CONTROL OF PLANT SPECIES

| Compound | Dosage (ppm) | A | B | C | D | E | F | G | H | I | J | K | L | M | N | O | P | Q | R | S |
|---|---|---|---|---|---|---|---|---|---|---|---|---|---|---|---|---|---|---|---|---|
| 1 | 750 | 40 | 90 | 80 | 100 | 80 | 10 | 0 | — | 80 | 0 | — | 0 | 0 | 0 | — | — | 0 | 0 | 0 |
| 2 | 700 | 0 | 0 | 0 | 40 | 0 | 0 | 20 | — | 0 | 0 | — | 0 | 0 | 0 | — | — | 0 | 0 | 0 |
| 3 | 500 | 50 | 90 | 35 | 95 | 85 | 90 | 15 | 100 | 95 | 0 | 0 | 80 | 0 | 0 | 0 | 0 | 10 | 0 | 0 |
| 4 | 2000 | 40 | 60 | 50 | 75 | 30 | — | 0 | 98 | 70 | 0 | 25 | 0 | 0 | 0 | 0 | 0 | 10 | 0 | 0 |

TABLE XVI-continued

POSTEMERGENT CONTROL OF PLANT SPECIES

| Compound | Dosage (ppm) | A | B | C | D | E | F | G | H | I | J | K | L | M | N | O | P | Q | R | S |
|---|---|---|---|---|---|---|---|---|---|---|---|---|---|---|---|---|---|---|---|---|
| 5 | 500 | 0 | — | 35 | 50 | 0 | — | 0 | 80 | 75 | 0 | 0 | 10 | 0 | 0 | 0 | 0 | 0 | 0 | 0 |
| 6 | 500 | 100 | 90 | 85 | 100 | 80 | 80 | 75 | 100 | 100 | 50 | 0 | 60 | 0 | 90 | 0 | 0 | 20 | 0 | 10 |
| 10 | 250 | 70 | 80 | 60 | 100 | 50 | — | 50 | 100 | 70 | 0 | 30 | 50 | 0 | 30 | 20 | 60 | 0 | 0 | 40 |
| 11 | 500 | 0 | 80 | 0 | 0 | 0 | 60 | 0 | 80 | 0 | 0 | 0 | — | 0 | 0 | 0 | 0 | 0 | 0 | 0 |
| 12 | 2000 | 0 | 30 | 0 | 75 | 20 | 70 | 0 | 100 | 0 | 0 | 0 | 0 | 0 | 0 | 0 | 0 | 0 | 0 | — |
| 15 | 2000 | 15 | — | 20 | 75 | 40 | 70 | 20 | 100 | 40 | 25 | 0 | 20 | 0 | 0 | 0 | 0 | 0 | — | 0 |
| 16 | 2000 | 0 | 85 | 50 | 100 | — | 60 | 80 | 100 | 85 | 0 | 20 | 0 | 0 | 0 | 50 | 60 | 35 | 0 | — |
|  | 1000 | 0 | 80 | 40 | 80 | 40 | 50 | 80 | 100 | 85 | 0 | 15 | 0 | 0 | 0 | 20 | 40 | 30 | 0 | 70 |
| 21 | 2000 | 0 | 30 | 35 | 30 | 0 | 30 | 0 | 100 | 50 | 0 | — | 0 | 0 | 0 | 0 | 0 | 0 | 0 | 0 |
| 23 | 1000 | 40 | 90 | 100 | 100 | 100 | 100 | 10 | 100 | 85 | 0 | 70 | 15 | 0 | 0 | 0 | 0 | 40 | 10 | 0 |
| 24 | 2000 | 40 | 60 | 45 | 40 | 0 | 0 | 0 | 100 | 70 | 0 | 0 | 0 | 0 | — | 0 | 0 | 0 | 0 | 0 |
| 26 | 2000 | 0 | — | 10 | 10 | 10 | — | 10 | 80 | 0 | 0 | 0 | 0 | 0 | 0 | 0 | 0 | 20 | 0 | 0 |
| 27 | 2000 | 20 | 0 | 25 | 20 | 0 | 0 | 0 | 40 | — | 0 | 20 | 0 | 0 | 0 | 0 | 0 | 0 | 0 | 0 |
| 28 | 2000 | 40 | — | 40 | 10 | 0 | — | 0 | 100 | 90 | 0 | 0 | 0 | 0 | 0 | 0 | 0 | 0 | 0 | 0 |
| 29 | 4000 | 10 | — | — | — | — | — | 20 | 40 | 50 | — | — | — | — | 0 | 0 | 30 | — | 0 | 0 |
| 30 | 2000 | 0 | — | 20 | 0 | 30 | 20 | 10 | 50 | 0 | 0 | 0 | — | 0 | 0 | 10 | 0 | 10 | 0 | 0 |
| 31 | 2000 | 0 | 75 | 0 | 0 | 0 | 60 | 30 | 0 | 0 | 0 | 0 | 0 | 0 | 0 | 0 | 0 | 0 | 0 | 0 |
| 32 | 2000 | 50 | 85 | 50 | 35 | 40 | 80 | 0 | 100 | 75 | 0 | 0 | 0 | 0 | 15 | 0 | 0 | 0 | 0 | 0 |
| 33 | 2000 | 0 | 20 | 30 | 0 | 0 | — | 0 | 80 | — | 0 | 0 | 0 | 0 | 0 | 50 | 0 | 0 | 0 | 0 |
| 34 | 4000 | 0 | — | — | — | — | — | 20 | 40 | 20 | — | — | — | — | — | 0 | 0 | — | 0 | 0 |
| 35 | 2000 | 20 | 70 | 75 | 25 | 0 | 0 | 0 | 50 | 100 | 0 | 0 | 20 | 0 | 0 | 60 | 0 | 0 | 0 | 0 |
| 36 | 2000 | 0 | — | 40 | 0 | 0 | — | 0 | 40 | 15 | 0 | 10 | 0 | 0 | 0 | 0 | 60 | 0 | 0 | 0 |
| 37 | 2000 | 35 | 80 | 70 | 80 | 20 | 75 | 40 | 100 | 60 | 0 | 0 | 0 | 0 | 0 | 50 | 60 | 0 | 0 | 80 |
| 38 | 2000 | 50 | — | 10 | 20 | 0 | — | 0 | 95 | 20 | 0 | 0 | 0 | — | 0 | 0 | 0 | 0 | 0 | 0 |
| 39 | 1000 | 0 | 80 | 0 | 20 | 0 | 0 | 0 | 80 | 40 | 0 | 0 | 0 | 0 | 0 | 0 | 0 | 0 | 0 | 0 |
| 40 | 4000 | 40 | — | — | — | — | — | 50 | 50 | 98 | — | — | — | — | 0 | 0 | 0 | — | 0 | 0 |
| 41 | 2000 | 30 | 100 | 20 | 0 | 15 | — | 0 | 90 | 45 | 0 | 0 | 0 | 0 | 0 | 0 | 0 | 0 | 0 | 0 |
| 42 | 2000 | 50 | 80 | 20 | 0 | 0 | 75 | 0 | 100 | 50 | 0 | 0 | 0 | 0 | 0 | 0 | 50 | 20 | 0 | 0 |
| 44 | 2000 | 0 | 70 | 40 | 50 | — | 0 | 0 | 35 | 0 | 0 | 0 | 0 | 0 | 0 | 0 | 0 | 0 | 0 | 0 |
| 47 | 500 | 0 | 70 | 0 | 0 | 0 | 0 | 0 | 100 | 0 | 0 | 0 | 0 | 0 | 0 | 0 | 0 | 0 | 0 | 0 |

So as to clearly illustrate the phytotoxic properties of the various active ingredients of the present invention applied preemergently, a controlled greenhouse experiment is described below.

EXAMPLE 16

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control are set forth in the table below. Control refers to the reduction in growth compared to the observed results of the same untreated species.

TABLE XVII

PREEMERGENT CONTROL OF PLANT SPECIES

| Compound | Dosage (lb/acre) | A | B | C | D | F | G | H | I | J | K | L | M | N | O | Q | R | P | S |
|---|---|---|---|---|---|---|---|---|---|---|---|---|---|---|---|---|---|---|---|
| 1 | 2.0 | 80 | 70 | 80 | 80 | 0 | 30 | 70 | 70 | 0 | 50 | 0 | 0 | 0 | 0 | 0 | 40 | 0 | 30 |
| 3 | 1.0 | 100 | 100 | 80 | 100 | 30 | 60 | — | 100 | 0 | 40 | 40 | 0 | 0 | — | 10 | 0 | 0 | 70 |
| 4 | 10.0 | 80 | — | — | — | — | 90 | 90 | — | — | — | — | — | 0 | 0 | — | 0 | 0 | — |
| 5 | 10.0 | 60 | — | — | — | — | 80 | 98 | 90 | — | — | — | — | 40 | 20 | — | 20 | 30 | — |
| 6 | 0.25 | 40 | 100 | 60 | 70 | 30 | 0 | 0 | 0 | 0 | 0 | 0 | 0 | 0 | 0 | 0 | 100 | 0 | 0 |
| 10 | 4.0 | 95 | 100 | 85 | 100 | 95 | 80 | — | 100 | 30 | 100 | 0 | 0 | 70 | — | 20 | 0 | 40 | 100 |
| 11 | 2.0 | 80 | 100 | 60 | 90 | 100 | 40 | — | 0 | 60 | 50 | 30 | 50 | 50 | — | 30 | 60 | 30 | 0 |
| 12 | 10.0 | 80 | — | — | — | — | 98 | 98 | 90 | — | — | — | — | 20 | 80 | — | 0 | 30 | — |
| 15 | 10.0 | 50 | — | — | — | — | 70 | 98 | 80 | — | — | — | — | 0 | 0 | — | 0 | 0 | — |
| 16 | 2.0 | 80 | 100 | 30 | 100 | 100 | 100 | — | 70 | 20 | 20 | 40 | 0 | 30 | — | 50 | 0 | 50 | 100 |
|  | 0.5 | 40 | 100 | 0 | 100 | 100 | 100 | — | 0 | 0 | 0 | 0 | 0 | 30 | — | 20 | 0 | 0 | 100 |
| 17 | 10.0 | 90 | — | — | — | — | 80 | 100 | 90 | — | — | — | — | 20 | 30 | — | — | 50 | — |
| 19 | 10.0 | 80 | — | — | — | — | 40 | 98 | 40 | — | — | — | — | 0 | 98 | — | 0 | 80 | — |
| 23 | 1.0 | 60 | 90 | 50 | 100 | — | 40 | 98 | 80 | 20 | 20 | 30 | 30 | 0 | 0 | 0 | 0 | 0 | 90 |
| 24 | 4.0 | 0 | 90 | 40 | 40 | 0 | 0 | — | 20 | 0 | 0 | 0 | 0 | 0 | — | 0 | 0 | 0 | 0 |
| 27 | 10.0 | 20 | — | — | — | — | 60 | — | 80 | — | — | — | — | 0 | 0 | — | 0 | 0 | — |
| 28 | 10.0 | 50 | — | — | — | — | 70 | 98 | 70 | — | — | — | — | 0 | 0 | — | 0 | 0 | — |
| 29 | 10.0 | — | — | — | — | — | 90 | 98 | 100 | — | — | — | — | 0 | 0 | — | 0 | 0 | — |
| 32 | 10.0 | 50 | — | — | — | — | 98 | 90 | 98 | — | — | — | — | 0 | 0 | — | 0 | 0 | — |
| 34 | 10.0 | 40 | — | — | — | — | 60 | 100 | 98 | — | — | — | — | 0 | 0 | — | 0 | 0 | — |
| 35 | 10.0 | 80 | — | — | — | — | 40 | 98 | — | — | — | — | — | 0 | 0 | — | 0 | 0 | — |
| 36 | 4.0 | 0 | 100 | 0 | 90 | 0 | 0 | — | 0 | 0 | — | 0 | 0 | 0 | — | 0 | 0 | 0 | 60 |
| 38 | 10.0 | 80 | — | — | — | — | 90 | 98 | 98 | — | — | — | — | 0 | 0 | — | 0 | 0 | — |
| 39 | 10.0 | 90 | — | — | — | — | 99 | 100 | 98 | — | — | — | — | 0 | 20 | — | 0 | 70 | — |
|  | 4 | 10 | 90 | 0 | 50 | 0 | 0 | — | 50 | — | — | — | — | 0 | — | 0 | 0 | 0 | 0 |
| 40 | 10.0 | 40 | — | — | — | — | 70 | 90 | 95 | — | — | — | — | 0 | 0 | — | 0 | 0 | — |
| 41 | 10.0 | 40 | — | — | — | — | 70 | 80 | 60 | — | — | — | — | 0 | 0 | — | 0 | 0 | — |

TABLE XVII-continued

| | Dosage | PREEMERGENT CONTROL OF PLANT SPECIES PLANT SPECIES | | | | | | | | | | | | | | | |
|---|---|---|---|---|---|---|---|---|---|---|---|---|---|---|---|---|---|
| Compound | (lb/acre) | A | B | C | D | F | G | H | I | J | K | L | M | N | O | Q | R | P | S |
| 42 | 4 | 100 | — | 80 | 100 | 30 | 50 | — | 100 | 10 | 80 | 50 | 50 | 50 | — | 30 | — | 10 | 100 |
| 47 | 1.0 | 30 | 100 | 20 | 90 | 100 | 50 | — | 30 | 0 | 0 | 0 | 0 | 0 | — | 0 | 0 | 0 | 80 |

I claim:
1. A compound having the formula

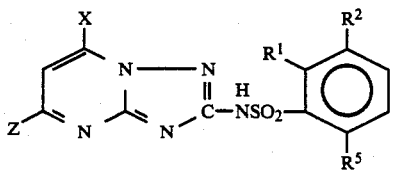

wherein $R^1$ represents halo, $-NO_2$, $-CF_3$, $-CN$ or $-COOR^7$, $R^2$ represents H, halo or $C_1$-$C_4$ alkyl, $R^5$ represents H, $C_1$-$C_4$ alkoxy or halo, $R^7$ represents H or $C_1$-$C_4$ alkyl and X and Z represent H, $CH_3$ or $C_1$-$C_2$ alkoxy groups with the proviso that X and Z cannot both be H.

2. Compound of claim 1 wherein X and Z are methyl.
3. Compound of claim 2 wherein $R^1$ and $R^5$ are Cl and $R^2$ is H.
4. A composition comprising an inert carrier in admixture with a herbicidally effective amount of a compound having the formula

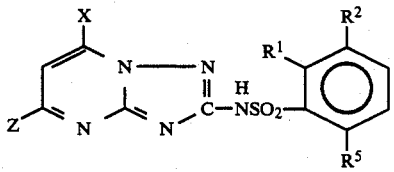

wherein $R^1$ represents halo, $-NO_2$, $-CF_3$, $-CN$ or $-COOR^7$, $R^2$ represents H, halo or $C_1$-$C_4$ alkyl, $R^5$ represents H, $C_1$-$C_4$ alkoxy or halo, $R^7$ represents H or $C_1$-$C_4$ alkyl and X and Z represent H, $CH_3$ or $C_1$-$C_2$ alkoxy groups with the proviso that X and Z cannot both be H.

5. Composition of claim 3 wherein X and Z are methyl.
6. Composition of claim 5 wherein $R^1$ and $R^5$ are Cl and $R^2$ is H.
7. Method of controlling undesired vegetation which comprises the application of a herbicidally effective amount of a compound having the formula

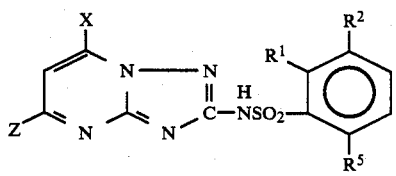

wherein $R^1$ represents halo, $-NO_2$, $-CF_3$, $-CN$ or $-COOR^7$, $R^2$ represents H, halo or $C_1$-$C_4$ alkyl, $R^5$ represents H, $C_1$-$C_4$ alkoxy or halo, $R^7$ represents H or $C_1$-$C_4$ alkyl and X and Z represent H, $CH_3$ or $C_1$-$C_2$ alkoxy groups with the proviso that X and Z cannot both be H.

8. Method of claim 7 wherein X and Z are methyl.
9. Method of claim 8 wherein $R^1$ and $R^5$ are Cl and $R^2$ is H.

* * * * *

UNITED STATES PATENT AND TRADEMARK OFFICE
CERTIFICATE OF CORRECTION

PATENT NO. : 4,822,404

DATED : April 18, 1989

INVENTOR(S) : William A. Kleschick

It is certified that error appears in the above-identified patent and that said Letters Patent is hereby corrected as shown below:

On cover page, in "Related U.S. Application Data", delete "Sec. No." and insert -- Ser. No. --;

On cover sheet, in "FOREIGN PATENT DOCUMENTS", delete "58-31894" and insert -- 48-31894 --;

Col. 1, line 22, "addition" has been misspelled;

Col. 1, line 54, "alkylthiocarbonyl" has been misspelled;

Col. 1, line 55, "containing" has been misspelled;

Col. 1, line 68, between "5" and "thiazolyl" insert a hyphen;

Col. 2, line 3, "2-benzoxazolyl" has been misspelled;

Col. 2, line 3, "2-benzimidiazolyl" has been misspelled;

Col. 2, line 8, after "haloalkoxy" insert a comma;

Col. 2, line 20, delete "acid" and insert -- acids --;

Col. 2, line 27, "readily" has been misspelled;

Col. 2, line 27, "available" has been misspelled;

Col. 5, line 58, "tertiary" has been misspelled;

Col. 5, line 67, "use" has been misspelled;

UNITED STATES PATENT AND TRADEMARK OFFICE
CERTIFICATE OF CORRECTION

PATENT NO. : 4,822,404
DATED : April 18, 1989
INVENTOR(S) : William. A. Kleschick It is certified that error appears in the above-identified patent and that said Letters Patent is hereby corrected as shown below:

Col. 6, line 36, after "with" delete "chloride" and insert -- chlorine --;

Col. 6, line 39, "outlined" has been misspelled;

Col. 6, line 46, delete "ester" and insert -- esters --;

Col. 10, line 2, "the" has been misspelled;

Col. 10, lines 16-22, change formula as follows:

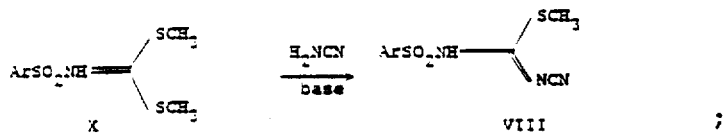

Col. 10, line 47, delete "mole" and insert -- mol --;

Col. 10, line 49, "temperature" has been misspelled;

Col. 11, line 2, "filtrate" has been misspelled;

Col. 11, line 40, "anhydrous" has been misspelled;

Col. 11, line 61, "(2-nitrophenylsulfonyl)" has been misspelled;

Col. 13, line 33, after "2.32;" delete "H" and insert -- N --;

UNITED STATES PATENT AND TRADEMARK OFFICE
CERTIFICATE OF CORRECTION

PATENT NO. : 4,822,404

DATED : April 18, 1989

INVENTOR(S) : William A. Kleschick

It is certified that error appears in the above-identified patent and that said Letters Patent is hereby corrected as shown below:

Col. 14, line 21; delete "285.5°" and insert -- 258.5° --;

Col. 14, line 30, delete "2.0" and insert -- 2.02 --;

Col. 20, in "TABLE IX", delete the heading "Elemental Analysis" and insert -- Elemental Composition --;

Col. 24, line 28, delete "to-";

Col. 24, line 37, after "group," "alkyl" has been misspelled;

Col. 24, line 44, delete "acid" and insert -- acids --;

Col. 26, line 2, "equally" has been misspelled;

Col. 26, line 43, delete "2-14" and insert -- 2-4 --.

Signed and Sealed this

Fourth Day of February, 1992

Attest:

*Attesting Officer*

HARRY F. MANBECK, JR.

*Commissioner of Patents and Trademarks*